(12) United States Patent
Dority et al.

(10) Patent No.: US 6,887,250 B1
(45) Date of Patent: May 3, 2005

(54) MULTIPLE BLADED SURGICAL KNIFE AND METHOD OF USE

(76) Inventors: Douglas B. Dority, 25 Castlerock Dr., Mill Valley, CA (US) 94941; Eli I. Zeevi, 2147 Newhall St., #137, Santa Clara, CA (US) 95050

(*) Notice: Subject to any disclaimer, the term of this patent is extended or adjusted under 35 U.S.C. 154(b) by 0 days.

(21) Appl. No.: 08/710,119

(22) Filed: Sep. 12, 1996

(51) Int. Cl.$^7$ ............................................ A61B 17/322
(52) U.S. Cl. ...................... 606/132; 606/133; 606/167; 30/305
(58) Field of Search ................................ 606/131, 132, 606/133, 167; 30/304, 305

(56) References Cited

U.S. PATENT DOCUMENTS

| | | | |
|---|---|---|---|
| 1,913,800 A | | 6/1933 | Farquhar |
| 1,977,902 A | | 10/1934 | Vermillion |
| 2,250,237 A | * | 7/1941 | Schwartzkopf .............. 30/304 |
| 3,452,754 A | * | 7/1969 | Stayer ......................... 606/167 |
| 3,488,843 A | * | 1/1970 | Tims ............................ 30/304 |
| 4,578,865 A | * | 4/1986 | Keller ......................... 30/304 |
| 5,026,385 A | | 6/1991 | Schutte et al. |
| 5,100,391 A | | 3/1992 | Schutte et al. |
| 5,431,671 A | | 7/1995 | Nallakrishnan |
| 5,447,516 A | | 9/1995 | Gardner |
| 5,456,010 A | | 10/1995 | Bryda |

FOREIGN PATENT DOCUMENTS

| | | |
|---|---|---|
| CA | 939133 | 1/1974 |
| DE | 1144437 | * 2/1963 |
| GB | 2530 | 10/1864 |
| GB | 1316 | 3/1883 |
| GB | 1334383 | * 10/1973 |
| WO | WO96/06566 | 3/1996 |

* cited by examiner

Primary Examiner—Michael H. Thaler
(74) Attorney, Agent, or Firm—Burns, Doane, Swecker & Mathis, L.L.P.

(57) ABSTRACT

A multiple bladed surgical knife for removing donor strips of hair-laden scalp tissue from a donor for hair graft transplantation to a donor. The knife includes a plurality of blades which are spaced apart by a plurality of spacers. The blades may advantageously shift longitudinally with respect to each other at a surgeon's discretion such that donor strips of consistent depth are obtained. In addition, the number of hair follicles which are destroyed during the removal process is minimized. In one embodiment of the present invention, the blade penetration depth is controlled via selectively sizing and shifting the plurality of spacers. In one particular embodiment, the blades and spacers may be shifted with the assistance of a pin, and in another embodiment, the knife includes a plurality of markings indicating a particular blade angle.

28 Claims, 6 Drawing Sheets

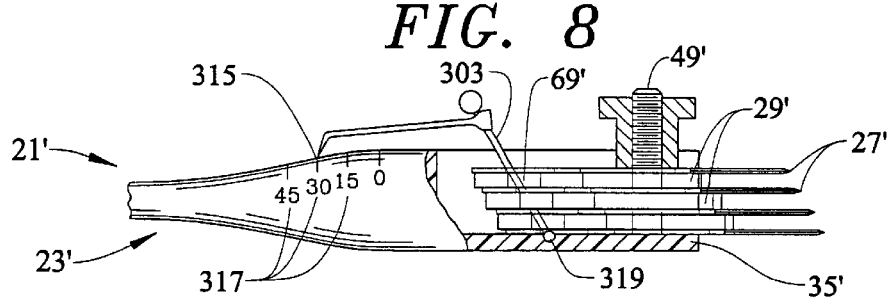
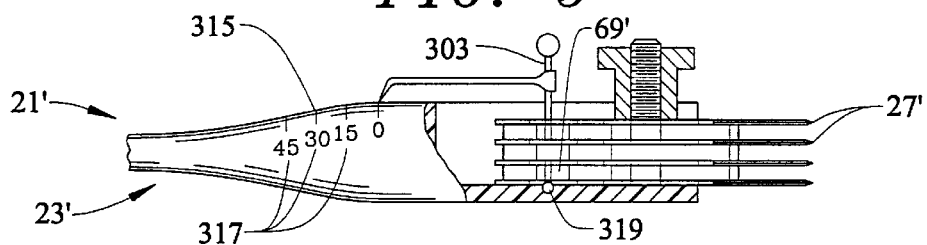
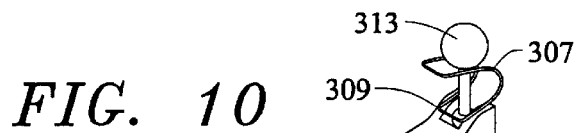
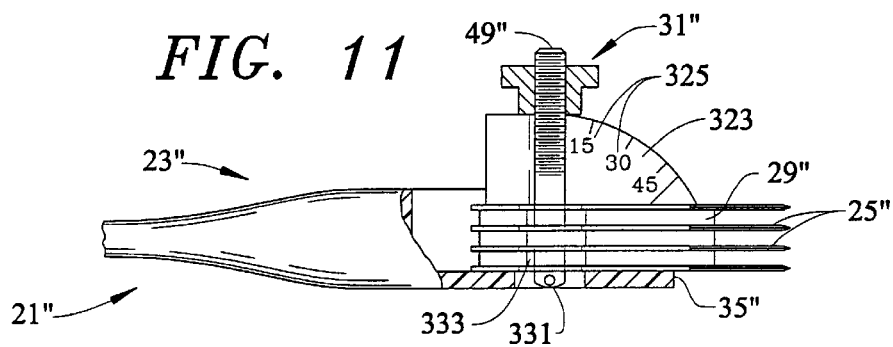
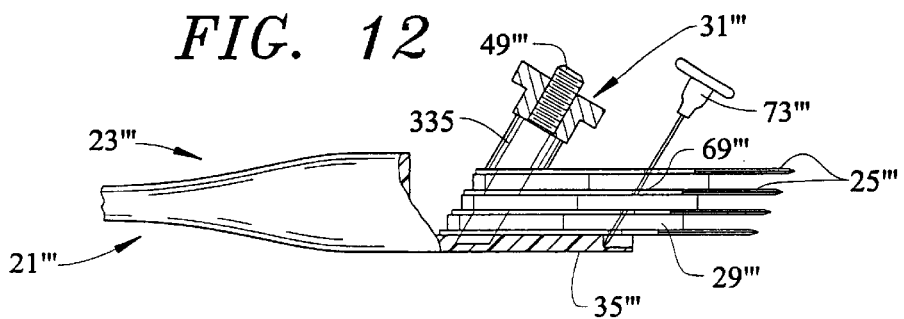

MULTIPLE BLADED SURGICAL KNIFE AND METHOD OF USE

BACKGROUND OF THE INVENTION

1. Field of the Invention

The present invention relates to surgical knives, and more particularly to multiple bladed surgical knives with adjustable blades used in hair transplantation procedures.

2. Description of the Related Art

Many hair transplantation procedures have been developed which transfer hair and living hair follicles from a donor to a donee. For example, a circular punch is commonly used to form a small diameter hole in the scalp of a donee.
Thereafter, a skin graft containing hair and follicles which has been removed from a donor is transplanted to the hole left by the punch. The size of the hole left by the punch often controls the number of hairs which may be transplanted in a single graft; usually, only a small number of hairs, such as 2 to 6 hairs are transplanted in a single graft. Sometimes, even a single hair is transplanted. Thus, a typical hair transplantation procedure requires a large number of grafts, which must be obtained from a donor. In some instances, hair is removed from and transplanted to the same individual.

Initially, grafts were obtained by carefully cutting sections of hair-laden scalp using a scalpel, which was a tedious and difficult procedure. In order to simplify the removal of grafts, knives with multiple parallel blades were developed such as the knife 100 depicted in FIG. 1A. These known knives permit removal of long strips of hair-laden skin from a donor. As illustrated in FIG. 1A, known multiple bladed knives 100 have three or more parallel blades 101 enabling removal of more than one donor strip of skin in a single operation. The blades 101 of the known knife 100 each have openings which receive a pair of pins 103, 105. One of the pins 105 is typically threaded and receives a nut 106 which secures the blades 101 to a blade handle 107. When used to obtain skin strips from a donor's scalp, the knife 100 is positioned perpendicular to the donor's scalp, inserted to the desired depth and drawn along a number of centimeters, producing the above described strips of hair-laden skin. These strips are then cut into the numerous individual grafts typically required for hair transplantation to a donee.

Hair customarily grows at an angle with respect to the surface of the scalp. Likewise, the hair follicles located below the skin are also at an angle with respect to the surface of the scalp. When removing strips of hair-laden skin, the knife edges of a multiple bladed knife which is positioned perpendicular to the donor's scalp often inadvertently destroy hair follicles located below the scalp because they are located within the blades' path below the skin even though the hair itself may not be within the blades' path above the skin. In some instances, only 20% of the hair follicles on a donor strip remain intact for successful transplantations.

Thus, surgeons removing strips of skin with multiple bladed knives such as the knife 100 often orient the blades parallel to the direction of hair and follicle growth to minimize the chance that follicles may be destroyed. By angling the knife blades parallel with the direction of hair growth, less hair follicles are destroyed when the knife blades are drawn through the scalp tissue. This procedure permits a surgeon to cut a larger number of individual skin grafts from fewer donor strips.

However, angling the knife 100 of FIG. 1A in such a manner generally produces undesirable results because angulation naturally forces some blades to penetrate the scalp further than others. More specifically, if the knife 100 is angled such that a lower surface 109 of the handle 107 is nearest the scalp, the blades closest to the lower surface 109 will penetrate the scalp further than the blades farthest from the lower surface 109. Such angled blades could penetrate the scalp too deeply, risking damage to adjacent follicles, and may unnecessarily injure the donor by cutting into the donor's skull. Likewise, too shallow blade penetrations are insufficient to properly remove the hairs and follicles.

Thus, knives with multiple parallel and staggered blades were developed, such as that disclosed in International Publication Number WO 96/06566 by Arnold et al., which is illustrated in FIG. 1B. The knife 200 of FIG. 1B includes parallel and staggered blades 201. The blades 201 are held in place by two pins 203, 205, which are at an angle with respect to the handle 207, rather than extending perpendicular therefrom. This configuration staggers the blade tips at a single angle with respect to the longitudinal axis of a blade handle 207. The staggering of the blades 201 at a fixed angle permits the blades to be introduced to the scalp at a constant angle such that each donor strip is uniform in depth.

Because the blades 201 are solely held in place by the pins 203, 205, and secured by the nut 206, the blades are generally unstable, especially when subjected to lateral, twisting, and longitudinal forces experienced during operation. This instability complicates the donor strip removal procedure.

A surgeon using such a staggered blade knife 200 begins the strip removal procedure by evaluating the direction of hair growth at the position where the incisions are initially to be started. The surgeon then chooses a multiple bladed knife 200, such as the knife shown in FIG. 1B, which has the same angle as that of the hairs. Next, the surgeon orients the position of the knife 200 so that the blades 201 are aligned and parallel with the hairs. Thereafter, the blades 201 are pressed into the scalp while maintaining the parallel orientation of the blades with the hairs.

Typically, the direction of hair growth with respect to the scalp changes in different areas of the scalp of a single donor. Because of these changes, the surgeon must continually re-evaluate the orientation of the hairs growing in the scalp. As the direction of the hairs changes, the surgeon must readjust the orientation of the knife 200 relative to the hairs such that the blades 201 remain generally parallel to the hairs at all times during translation. This procedure must be done to prevent damage to a large number of follicles located within and outside the donor strip.

Regrettably, once the surgeon readjusts the orientation of the fixed angle knife 200 to prevent damage to follicles, the depth of the donor strip changes. Because the angle of the hair often changes dramatically throughout the scalp, a surgeon typically will select an area of the scalp for donor strip removal and then choose a knife with staggered blades approximating the average angle in the selected area.
However, the average orientation of the hair on the selected scalp area varies on different individual's heads and at different areas of the head. To properly address the average angle of the hair in a selected area, the surgeon must have a plurality of knives of numerous fixed blade angles to match the different average hair angles in order to maintain the uniform thickness of the donor strips and to prevent damage to the hair follicles—an extremely impractical solution to a reoccurring problem.

When using the knives 100, 200, the surgeon must continually approximate the depth that each of the blades should penetrate the scalp to achieve adequate depth penetration so that the entire follicle is removed while preventing contact with the skull. This depth approximation is difficult for surgeons inexperienced in donor strip removal operations. Because of the uncertainty associated with estimating the blade penetration depth, a surgeon may injure the donor by cutting too deeply into the scalp. Likewise, if the blades penetrate to deeply in an angular direction, the surgeon may unintentionally damage the follicles in the donor strip. Furthermore, the surgeon may insufficiently penetrate the surface of the scalp such that the hair follicles are not removed with the donor strip.

The previous described problems associated with current multiple bladed surgical knives limits their range of use. Human hair grows from the scalp in a variety of directions from one area of the scalp to another. Because of the above identified problems of current multiple bladed surgical knives, it is tedious and difficult to remove donor hair strips of constant depth without damaging a vast number of follicles in the donor strip. The previously described constraints of current multiple bladed surgical knives has created a need for a solution.

OBJECTS AND SUMMARY OF THE INVENTION

A primary object of the invention is to provide a multiple bladed surgical knife with a shifting mechanism which permits longitudinal shifting of the forward ends of the blades with respect to each other and with respect to a base.

Another object of the invention is to provide a multiple bladed surgical knife having blades with forward ends which define a line; the line defining an adjustable angle with respect to a longitudinal axis of the blades.

Another object of the invention is to provide a multiple bladed surgical knife which is capable of removing strips of hair-laden skin from a donor without destroying a majority of the hair follicles.

Still another object of the invention is to provide a multiple bladed surgical knife which is capable of removing donor strips of hair-laden skin of uniform depth.

Yet another object of the invention is to provide a multiple bladed surgical knife which permits a surgeon to control the depth of blade penetration.

Still another object of the invention is to provide a multiple bladed surgical knife which permits longitudinal shifting of the forward ends of the blades with respect to each other and prevents the blades from rotating with a forward wall.

According to the present invention, the foregoing and other objects are obtained by a multiple bladed surgical knife which includes blades that may advantageously shift longitudinally with respect to each other at a surgeon's discretion. The knife includes a handle having a distal end and a proximal end, the distal end including a base, a plurality of movable blades removably mounted on the base of the handle, each of the blades having a longitudinal axis and a sharpened forward end, a plurality of spacers spacing the blades from each other, a securing member removably securing the blades to the handle, a shifting mechanism for longitudinally shifting the blades with respect to each other to a plurality of blade positions, the forward ends of the blades forming a first line at a first blade position and a second line at a second blade position.

In accordance with another aspect of the present invention, the multiple bladed surgical knife includes a base, a plurality of parallel blades, means for securing the blades to the base, and means for shifting a longitudinal position of the blades with respect to each other and with respect to the base.

In accordance with another aspect of the present invention, a method of removing hair-laden tissue from a donor for transplantation includes the steps of providing a multiple bladed surgical knife having a base, a plurality of blades, means for securing the blades to the base, and means for shifting a longitudinal position of the blades with respect to each other and with respect to the base; determining a hair angle between a direction of hair growth and a line perpendicular to a scalp; shifting the blades to a plurality of positions whereby a line formed by a forward end of each of the blades is orientated at a blade angle with respect to a line perpendicular to a longitudinal axis of the knife, the blade angle being substantially equal to the hair angle; inserting the blades into the scalp at a direction parallel to the direction of hair growth; translating the blades through the scalp; and removing a plurality of hair-laden tissue strips from the scalp.

Still other objects and advantages of the present invention will become readily apparent to those skilled in the art from the following detailed description, wherein only the preferred embodiments of the present invention have been illustrated. As will be realized, the invention is capable of other and different embodiments, and its several details are capable of modification in various obvious aspects, all without departing from the invention. Accordingly, the drawings and description are to be regarded as illustrative in nature, and not restrictive.

BRIEF DESCRIPTION OF THE DRAWINGS

FIG. 8 is a partial cross-sectional side view of a second embodiment of the present invention in a shifted position;

FIG. 9 is a partial cross-sectional side view of the second embodiment of the present invention in an unshifted position;

FIG. 10 is a perspective view of an exemplary shifting mechanism of the present invention;

FIG. 11 is a partial cross-sectional side view of a third embodiment of the present invention; and FIG. 12 is a partial cross-sectional side view of a fourth embodiment of the present invention.

DETAILED DESCRIPTION OF THE PREFERRED EMBODIMENTS

Figure 1A:
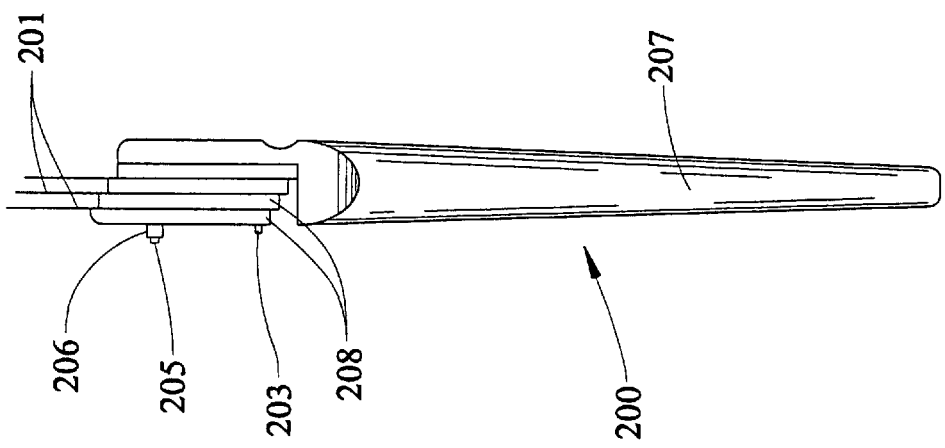
FIG. 1A is a side view of a prior art multiple bladed surgical knife.

FIGS. 2 through 11 depict exemplary embodiments of the present invention which all include a multiple bladed surgical knife 21 for removal of hair-laden skin strips from a donor's scalp. These donor strips which are removed from a donor's scalp are cut into individual grafts for transplantation to a donee's scalp. An exemplary embodiment of the multiple bladed surgical knife 21 depicted in the perspective view of FIG. 2 and in the exploded view of FIG. 3 includes a handle 23 and a plurality of blades 25. The blades 25 each have a sharpened forward end 27 and are spaced apart from each other by a plurality of spacers 29. A securing member such as a nut 31, for example, secures the blades 25 to the handle 23. As will be described in detail below with reference to FIGS. 4A and 4B, the blades 25 may advantageously shift longitudinally with respect to each other at a surgeon's discretion such that the forward ends 27 of the blades may change positions in a unique manner. This adjustability permits removal of donor strips of consistent depth while minimizing the number of hair follicles that are destroyed during donor strip removal.

Figure 2:
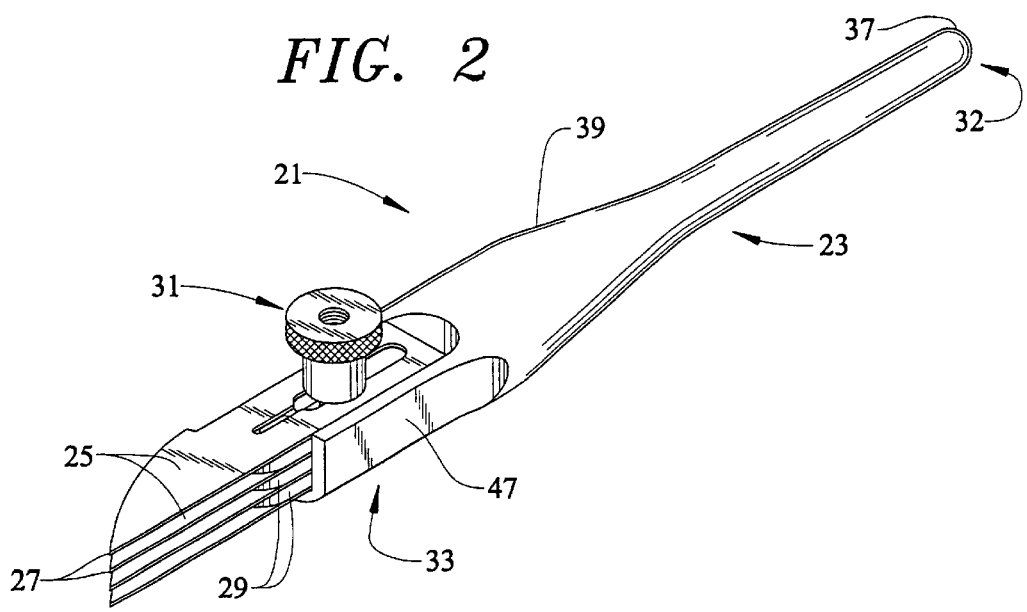
FIG. 2 is a perspective view of one embodiment of the present invention.
Figure 3:
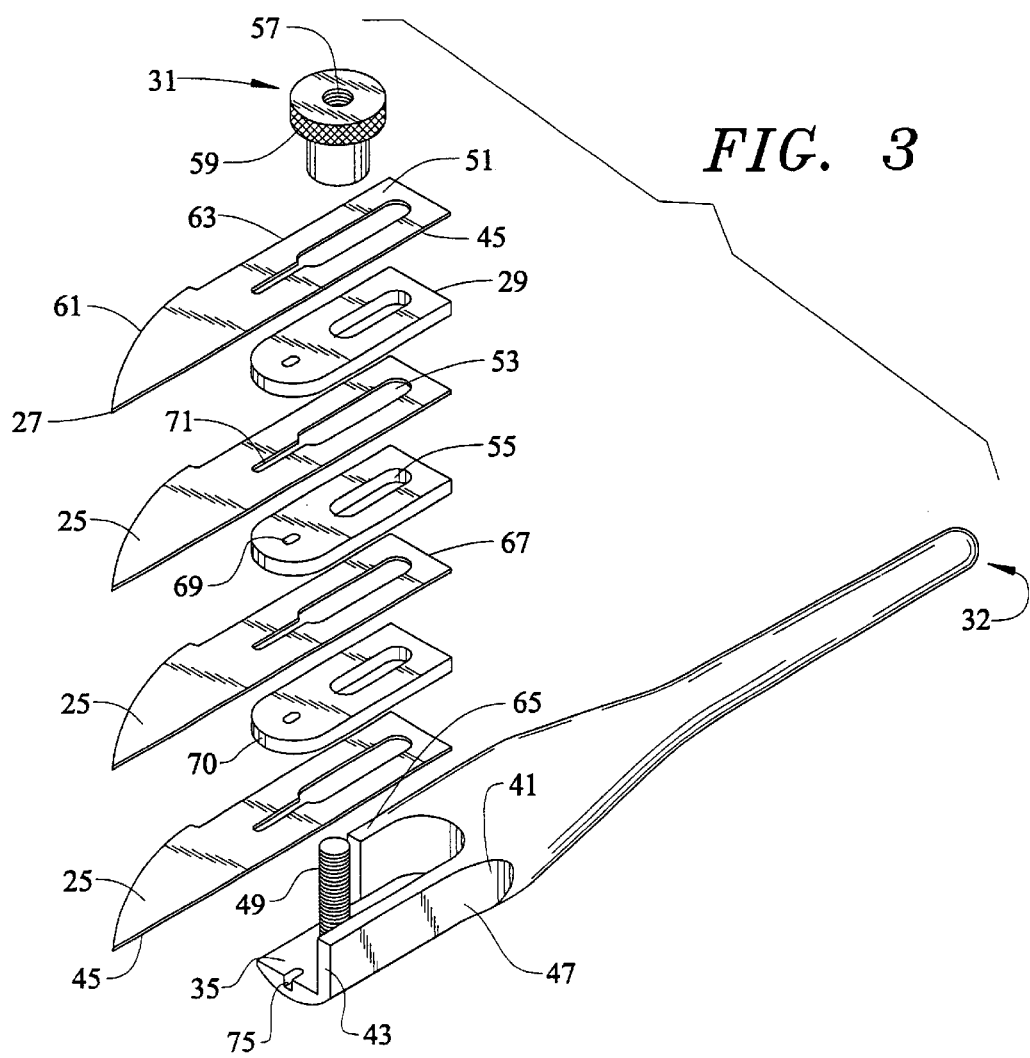
FIG. 3 is an exploded perspective view of the embodiment of FIG. 2.

Referring now to FIGS. 2 and 3, an embodiment of the present invention includes a multiple bladed surgical knife 21 comprising a handle 23 having a proximal end 32 and distal end 33. Because the knife 21 is used in surgical environments, the handle 23 is preferably made of stainless steel which is non-corrosive, easy to clean, and provides proper knife balance. Although stainless steel is the preferred material of the handle 23, other non-corrosive materials are contemplated such as various plastics and resins. The proximal end 32 of the handle 23 includes a smooth and tapered end surface 37 which prevents the handle 23 from unintentionally puncturing items during surgery.

The handle 23 includes a tapered portion 39 between the proximal end 32 and the distal end 33. The tapered portion 39 preferably gives the knife a comfortable ergonomic feel during use in surgery.

FIG. 3 illustrates most clearly the distal end 33 of the knife handle 23 including a recess 41 for receiving the plurality of blades 25 and the plurality of spacers 29. The blades 25 are preferably a standard stainless steel type blade commonly used in the surgical industry, and are relatively thin, as compared to the spacers 29. FIGS. 2 and 3 illustrate that when the blades 25 are placed in the recess 41, the spacers 29 are located between the blades in an alternating manner. Locating the spacers 29 in this manner separates the blades 25 from each other at a predetermined distance transverse to the longitudinal axis of the blades. The spacer thickness varies from 0.25 to 5.0 millimeters, preferably from 0.5 to 3.5 millimeters, but may vary outside this range depending upon a surgeon's needs. In another embodiment, which is not depicted, the spacer 29 may be the base 51 of the blade 25 itself such that the blades are spaced apart by the thickness of the blades at their base. Thus, the blades 25 may be spaced apart solely by the thickness of the individual spacers 29, solely by the thickness of the blade bases 51, or by the both the spacer and base thicknesses.

FIG. 3 illustrates that the blades 25 each contain an elongated rear opening 53 extending in the longitudinal direction of the blades. The spacers 25 include an elongated bolt opening 55 extending in the longitudinal direction of the spacers. These two openings 53 and 55 in each of the blades and spacers are adapted to receive a bolt 49 which is attached to a base 35 at the distal end 33 of the handle 23. The base 35 forms the bottom of the recess 41. The base 35 is substantially flat and preferably perpendicular to the inner surface of a forward wall 43 of the recess 41.

In the embodiment of the present invention depicted in FIGS. 2 and 3, the bolt 49 preferably extends perpendicularly to the base 35 and, as shown in FIG. 2, receives a nut 31. The nut 31 has female threads 57 adapted to receive the male threads of the bolt 49. The nut 31 also has an enlarged knurled exterior portion 59 with a series of small grooves and ridges to aid the surgeon in gripping and twisting the nut.

Thus, in assembling the knife 21, a first bottom blade 25 is oriented such that the opening 53 receives the bolt 49. The first blade 25 is then lowered into the recess 41 and placed on the base 35 such that a top edge 45 of the blade 25 is immediately adjacent an inside surface of the forward wall 43. The blades 25 each have a cutting edge 61 which curves from a bottom edge 63, located opposite the top edge 45, to the blade forward end 27. The blades 25 are oriented in the recess 41 such that the cutting edge 61 faces generally away from the inside surface of the forward wall 43.

Next, a first spacer 29 is oriented such that the bolt opening 55 of the spacer receives the bolt 49. The spacer is then lowered into the recess 41. The recess is preferably shaped and the bolt 49 is preferably located such that the spacers 29 and blades 25 fit squarely within the area between the forward wall 43 and a rearward wall 65. Thus, once the spacers 29 and blades 25 are placed within the recess 41, there is minimal room for rotation of the spacers and blades about the bolt 49. This configuration minimizes movement of the blades 25 during surgery.

The forward wall 43 abuts against the top edge 45 of the blades 25 and a corresponding top edge of the spacers 29. This abutting relationship prevents the blades 25 and spacers 29 from rotating about the bolt 49, especially when the blades and spacers are in a shifted position. Thus, when the blades 25 are translated through the scalp, the forward wall 43 supports the blades.

After the first blade 25 and spacer 29 are placed in the recess 41 in the manner described above, additional blades and spacers may be similarly located, a number of which depends on a surgeon's preference. As shown in FIGS. 2 and 3, one embodiment of the present invention has four blades 25 and three spacers 29. This configuration will produce three strips of hair-laden donor strips. However, any number of spacers 29 and blades 25 may be used and still be within the scope of the present invention.

Once the chosen number of blades 25 and spacers 29 have been located within the recess 41, the blades are then secured in place by a securing member, which in one embodiment of the present invention is the nut 31 and bolt 49 illustrated in FIGS. 2 and 3. Although a nut 31 and bolt 49 are the preferred means of securing the blades 25 and spacers 29 to the handle 23, a number of different means for securing the blades to the handle are contemplated by the present invention. For example, the blades may be held in place by any securing member or means for securing, such as self tapping screws, wood screws, machine screws, split screws, any nut and bolt configuration, pressure clasps, snaps, buckles, pins, latches, straps, or snaps. The nut 31 and bolt 49 are preferred because a surgeon may easily and dependably remove, loosen or tighten the nut and blades 25 on demand.

As shown in FIG. 2, the stacked blades 25 are parallel to each other because the spacers 29 and blades are preferably of uniform thickness. Thus, each of the blade forward ends 27 are located the same distance from each other along a line perpendicular to the blades, which results in uniform donor strip thicknesses.

FIG. 2 illustrates that the blades 25 may be positioned such that the blade forward ends 27 are all located along a common line. In one instance depicted in FIG. 2, the blades 25 form a line perpendicular to the longitudinal axis of the handle 23; this is called the zero degree position. Because the blades are preferably identical, when the blades 25 are located in the zero degree position, the back edges 67 of the blades are all located at the same position in the longitudinal direction of the handle 23, as are the blade forward ends 27.

When the blades 25 of the knife 21 are secure in the zero degree position, the knife 21 functions the same as the knife of FIG. 1A. In contrast to the present invention, the knives of FIGS. 1A and 1B have a series of pins 103, 105, and 203, 205 holding the blades 101, 201, respectively, in one stationary position such that the blades do not move longitudinally with respect to one another.

Figure 4A:
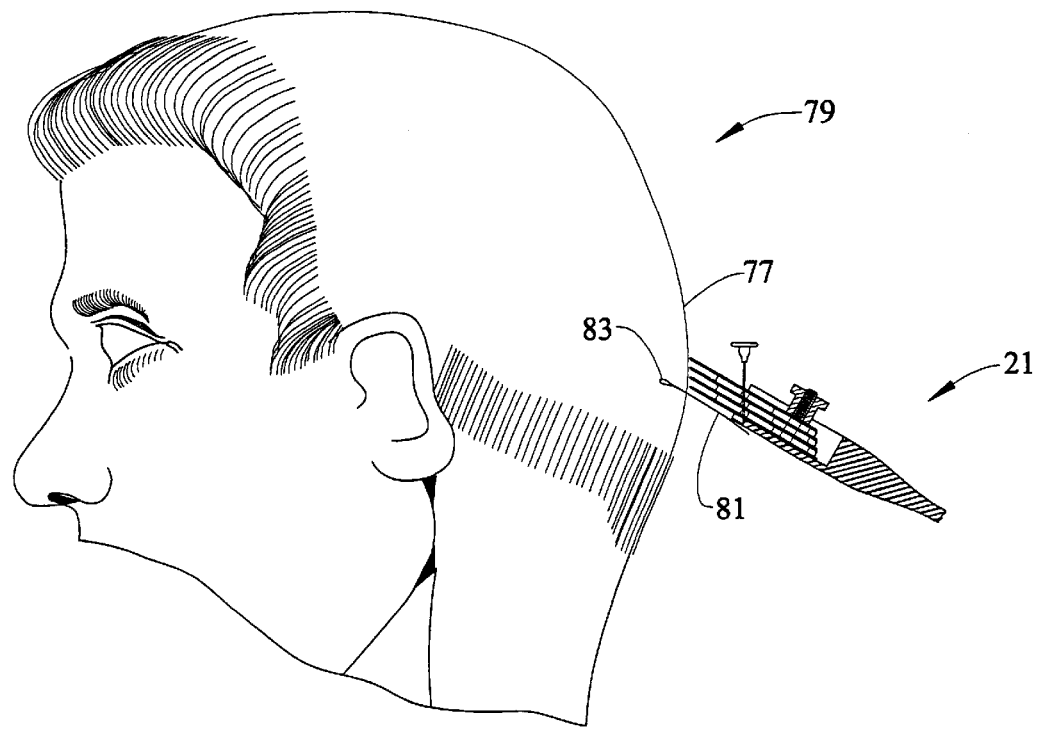
FIG. 4A is a cross-sectional side view of the embodiment of FIG. 2 in use.
Figure 4B:
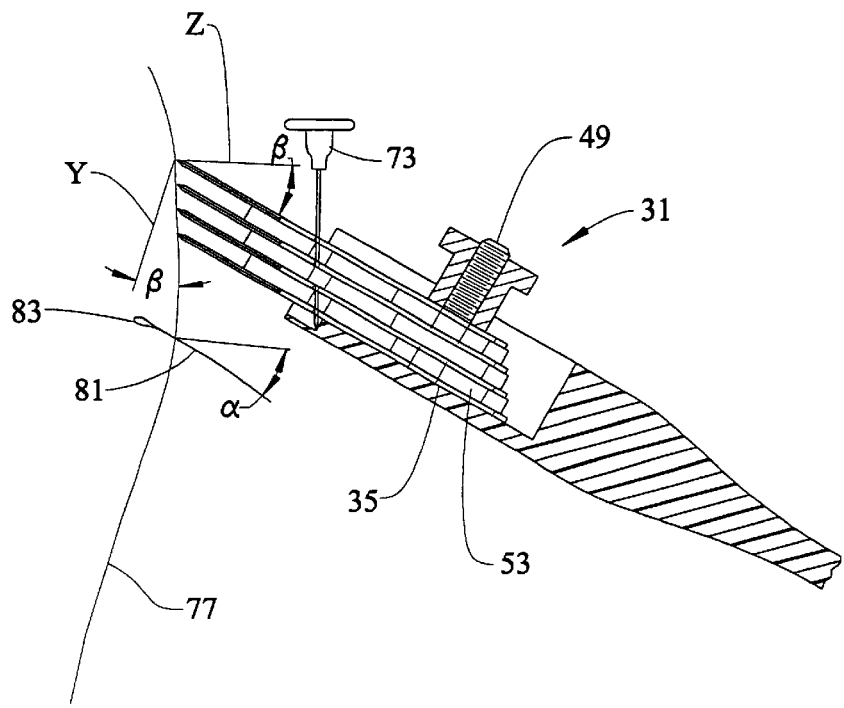
FIG. 4B is an enlarged view of FIG. 4A.

As illustrated in FIGS. 4A and 4B, an embodiment of the present invention permits the blades 25 to be longitudinally shifted with respect to each other to a plurality of positions whereby the forward ends or tips 27 of the blades form a plurality of different angled lines. For example, one line is formed in the zero degree position illustrated in FIG. 2 and a second line is formed at the angled position of FIGS. 4A and 4B. This shifting is accomplished by a shifting mechanism which is further described hereinafter.

The rear openings 53 of the blades 25 and the bolt openings 55 of the spacers 29 are sized to receive the bolt 49, but are also sized such that the spacers and the blades may longitudinally shift along the bolt. Thus, each of the blades 25 and the spacers 29 may be shifted to any number of longitudinal positions between the two extreme positions permitted by the rear opening 53 and the bolt opening 55.

As illustrated in FIG. 4B, the blade ends 27 may be positioned to form a line at a blade angle β with respect to a line y perpendicular to the planes of the blades and the spacers. The blade angle β may also be measured between a line z perpendicular to the line formed by the blade ends 27, and the plane of the blades. The range of blade angles β is from 0 to 75 degrees, preferably 0 to 45 degrees. The largest blade angle β permitted depends upon the size of the bolt 49, the bolt opening 55, and the rear opening 53, which may be any variety of dimensions and still be within the present invention.

As illustrated in FIG. 3, according to one embodiment of the invention, the base 35 at the forward edge of the recess 41 includes an indentation 75. Further, the spacers 29 have an additional pin opening 69, and the blades 25 have an additional elongated forward opening 71. Both openings 69 and 71 are adapted to receive a pin 73 depicted in FIGS. 4A and 4B. Although the embodiment of FIG. 3 depicts that the pin opening 69 is an elongated circular opening, it need not be shaped precisely so. For example, the bolt opening 55 and the pin opening 69 may be one continuous opening, similar to the openings 53 and 71 in the blades 25. Likewise, the openings 53 and 71 in the blades 25 may be shaped and size similar to the openings 55 and 69 in the spacers 29. The shape and size of the openings 53, 55, 69 and 71 may vary, assuming such permit the blades 25 to shift, and still fall within the bounds of the present invention.

When the blades 25 are placed into the knife recess 41 and secured to the knife 21 by the nut 31 in the zero degree position, the pin 73 may then be vertically placed through the forward openings 71 and the pin openings 69 such that a tip of the pin rests in the indentation 75 depicted most clearly in FIGS. 3 and 4B. Thereafter, the pin 73 is angled with respect to the longitudinal axis of the knife 21 such that the blades 25 and spacers 29 longitudinally shift distally with respect to each other and with respect to the base 35 as the pin is rotated in the longitudinal direction of the knife.

Thus, FIGS. 4A and 4B illustrate that the pin 73 and the openings 53, 55, 69 and 71 cause the blade ends or tips 27 to longitudinally shift to a plurality of positions in one embodiment of the present invention. The pin opening 69, the forward opening 71, the pin diameter, pin length, and indentation 75 size are all sized such that above described range of blade angles β may be achieved by rotating the pin 73 about the pin tip in the indentation. These aforementioned sizes may be in any variety of combinations and are easily determined by experimentation or geometrical design, as is commonly known in the art. The pin 73 which is employed for shifting the blades may be a conventional hypodermic needle.

Once the blades 25 are moved into an angled position as illustrated in FIGS. 4A and 4B, the surgeon need only retighten the nut 31, securing the blades 25 in the new angled position. The adjustability of the blades 25 provides many advantages as will be described below.

FIGS. 4A and 4B illustrate one of the many advantages of using an exemplary embodiment of the present invention. As depicted in FIGS. 4A and 4B, hair 81 and hair follicles 83 grow at an angle α with respect to a line perpendicular to the scalp. Because of this angling of the hair, a surgeon must carefully position the longitudinal axis of the multiple bladed knife 21 at an angle substantially equal to the angle α of the hair 81 such that the knife and hair are generally parallel. By doing this, the percentage of hair follicles 83 destroyed under the skin is minimized when a surgeon cuts the donor strips from the scalp 77; if this is not done, the blades 25 may destroy a majority of the hair follicles, which then requires that more donor strips be removed to obtain the necessary number of grafts for the resulting hair transplantation operation.

However, once the knife 21 of FIG. 2, having the blade forward ends 27 in the zero degree position (where the blade angle β equals zero degrees), is angled parallel with the hair growth and inserted into the scalp 77, some blades 25 will penetrate the scalp further than others. Thus, it is advantageous to insert the pin 73 into the openings 71 and 69, and then longitudinally shift the blade tips 27 such that the line formed by the blade tips forms a blade angle β substantially equal to the hair angle α.

By angling the blades at the blade angle β and angling the knife 21 at an angle generally parallel with the hairs 81, donor strips of uniform depth may be removed without damaging the follicles 83 or injuring the donor 79. Furthermore, when the surgeon selects a section of hair for donor strip removal which has an average hair angle α different than a previous area, the surgeon may conveniently readjust the blade angle β in the manner described above. Readjustment may be completed between separate donor strip removal operations. Hence, a surgeon may remove donor strips using only a single knife 21, which can accommodate a multitude of hair angles α, while also minimizing hair follicle 83 damage and keeping the donor strips a consistent depth.

Figure 5:
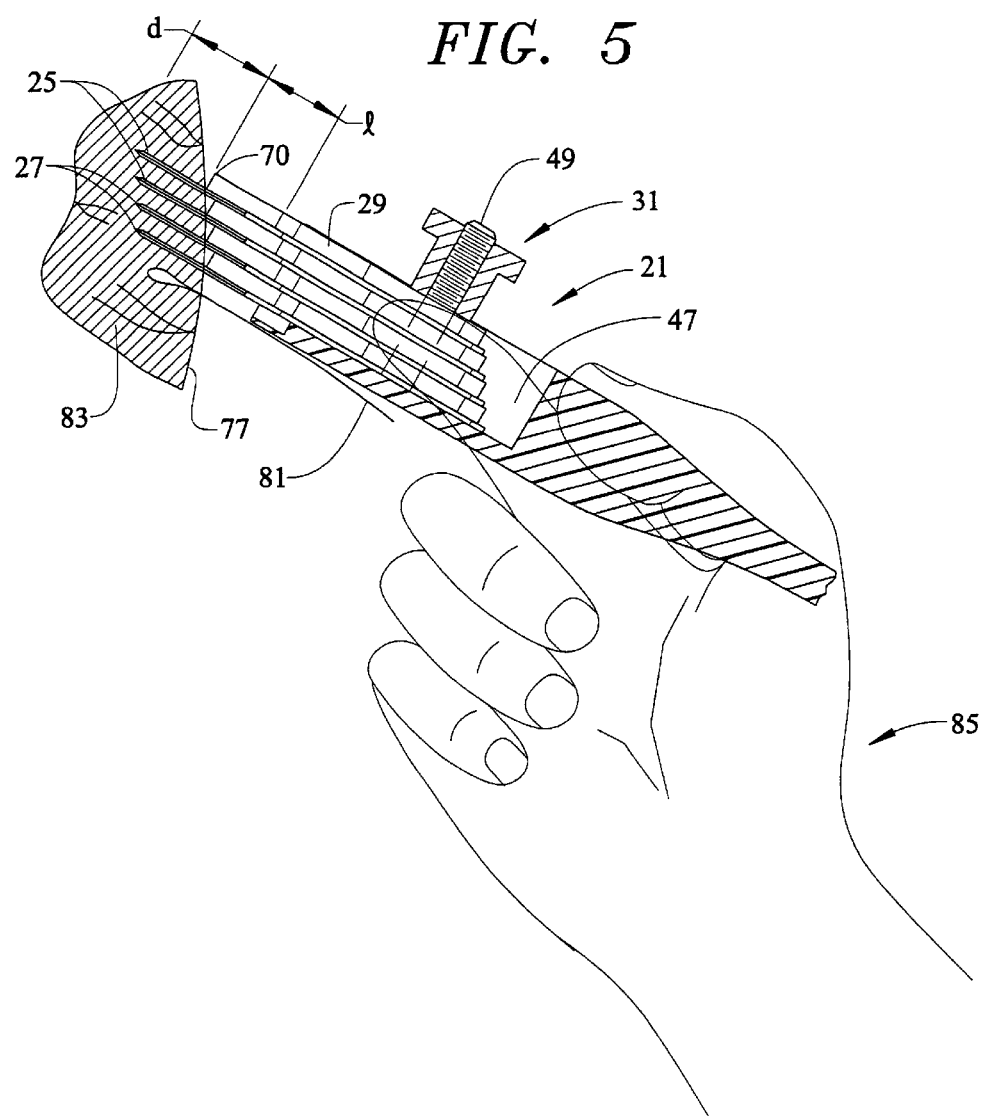
FIG. 5 is a cross-sectional side view of the embodiment of FIG. 2 during penetration of the scalp, taken through the center of the knife.

FIG. 5 illustrates an exemplary embodiment of the present invention in use during the donor strip removal procedure. The knife is preferably oriented such that the blades 25 are parallel to the hair 81. The blade angle β, also more clearly illustrated in FIG. 4B, is substantially equal to the hair angle α. As such, the blades 25 are each located at a common blade depth d, as depicted in FIG. 5.

Figure 1B:
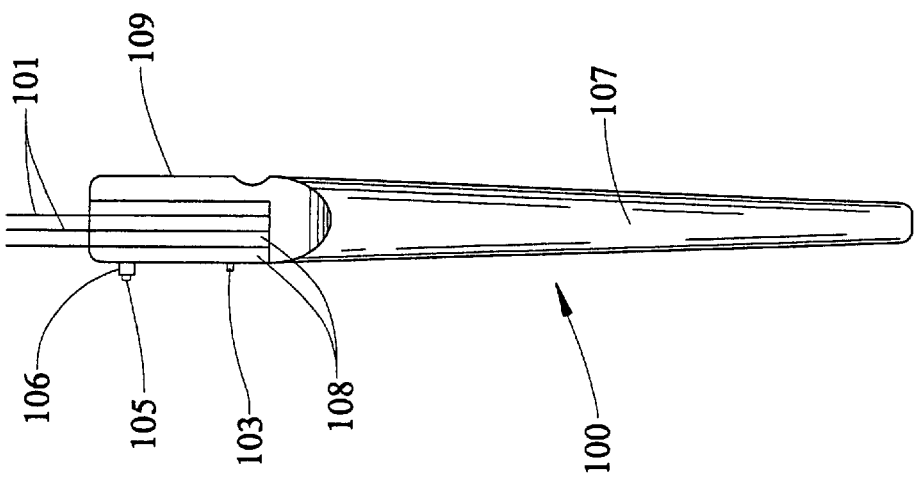
FIG. 1B is a side view of a prior art multiple bladed surgical knife with staggered blades.

Ordinarily, a surgeon using a common multiple bladed knife, such as those depicted in FIGS. 1A and 1B, must estimate the depth d that the blades penetrate the scalp 77.

It is very difficult to estimate exactly how deep the blades 20 penetrate the scalp, especially for an inexperienced surgeon. Proper estimation of the blade penetration depth d is important because (1) the donor strips are eventually cut into individual grafts which must be inserted into a hole in a donee's scalp of an equal depth, (2) the blades 25 must not penetrate beyond the fatty tissue of the scalp into the skull, and (3) the forward ends 17 of the blades must penetrate the scalp beyond the depth of the follicle 83.

By using an embodiment of the present invention depicted in FIG. 5, the surgeon need not estimate the blade penetration depth d. As illustrated in FIG. 5, the spacers 29 may be of a configuration such that when the blades 25 are inserted into the scalp 77, the forward ends 70 of the spacers 29 will abut against the scalp 77, preventing further penetration of the blades 25. The spacers 29 have a length l between the opening 69 for receiving the pin 73 and the forward end 70 of the spacers. The length l is sized to limit the penetration depth d of the needle 25 from 2 to 10 millimeters, preferably 5 to 8 millimeters. The depth limiting function of the spacers 29 provides a benefit which permits the surgeon to concentrate on the knife and blade orientation, without being entirely concerned with the blade penetration depth d.

FIG. 5 also depicts the orientation of the knife 21 with respect to a surgeon's hand 85. Located on the outer surface of the forward wall 43 is a finger rest 47, better illustrated in FIGS. 2 and 3, which is preferably shaped to receive the index finger of a surgeon. The finger rest 47 is the surface on which a surgeon applies pressure to the knife 21 and to the blades 25 located immediately thereunder to draw the blades through the scalp.

More clearly illustrated in FIGS. 2 and 3, the top edge 45 of the blades 25 is preferably adjacent to the inside surface of the wall 43, which assists in holding the blades in their shifted locations when the blades are subjected to cutting forces. Thus, by virtue of the location of the finger rest 47, pressure from a surgeon's finger during the donor strip removal process presses the blades 25 against the inside surface of the wall 43 and helps hold the blades 25 in position during use. Furthermore, the finger rest 47 and other flat surfaces of the knife prevent the knife 21 from rolling when placed on a flat surface.

Although the pin 73 may be used to shift the longitudinal positions of the blades 25, the blades may be shifted in other ways. For example, FIGS. 6 and 7 illustrate an alternative embodiment of the present invention in which the blade angle β is adjusted by an adjustment assembly 84.

Figure 6:
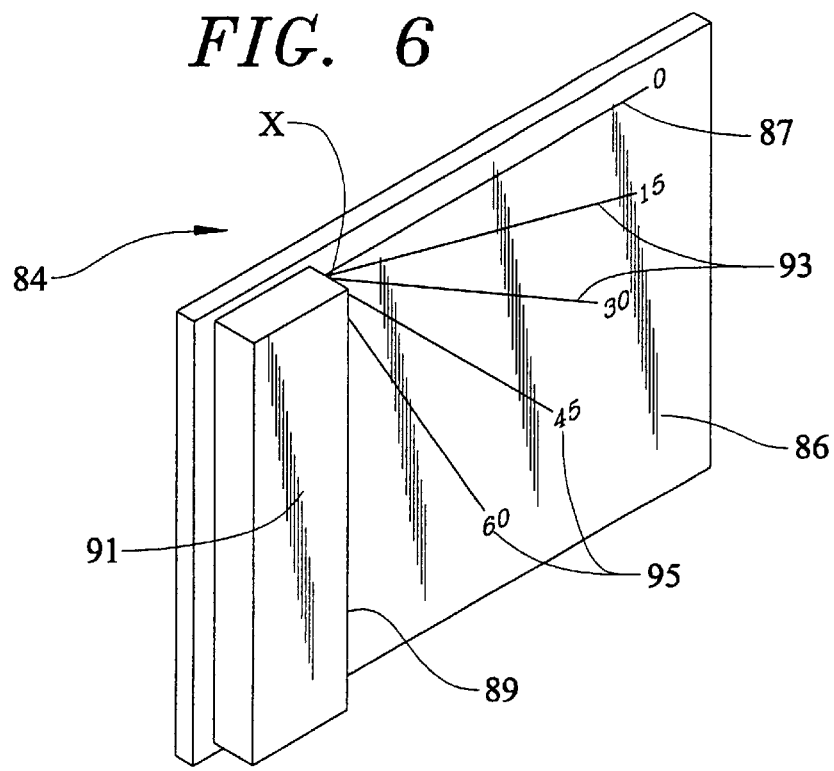
FIG. 6 is a perspective view of an adjustment assembly of the present invention.

FIG. 6 depicts an angle adjustment assembly 84. The adjustment assembly 84 has a forward face 86 having a substantially rectangular shape and a base line 87, which is located on the top of the forward face 86 in this particular embodiment. A raised edge 89 which is perpendicular to the base line 87 is provided by a rectangular block 91. The base line 87 meets the raised edge 89 at an origin X. A plurality of angled indicator lines 93 are located on the forward face 86 between the base line 87 and the raised edge 89 and radiating from the origin X. The indicator lines 93 indicate a plurality of angles between the base line 87 and the raised edge 89. Because the raised edge 89 and the base line 87 are perpendicular to each other, the angled indicator lines 93 designate angles between zero degrees at the base line 87 and 90 degrees at the raised edge 89.

Figure 7:
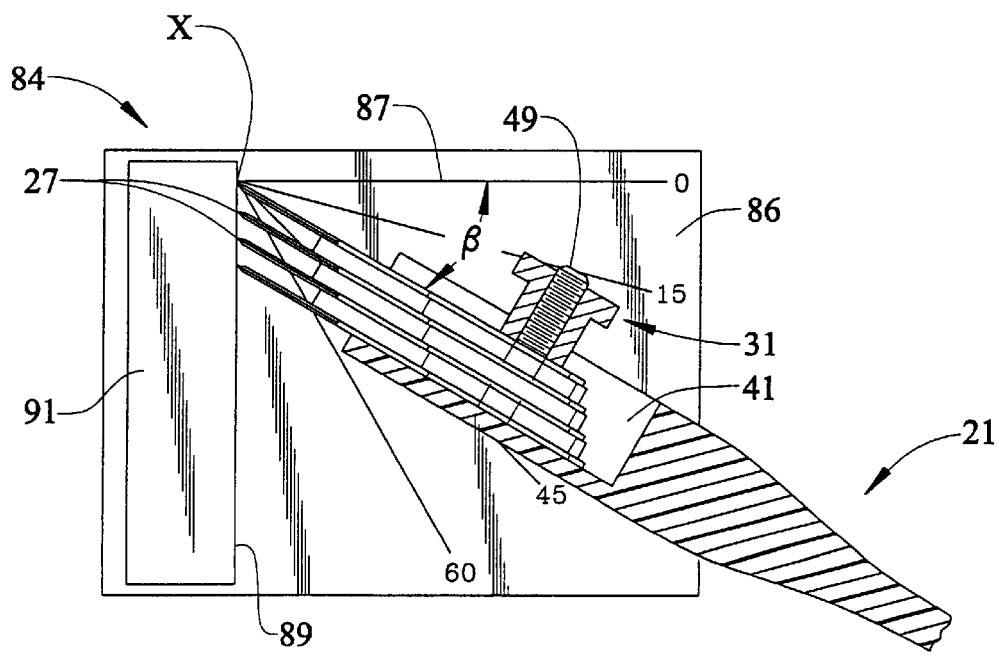
FIG. 7 is a plan view of the adjustment assembly of FIG. 6 and a cross-sectional side view of the embodiment of FIG. 2.

As depicted in FIGS. 6 and 7, a total of four indicator lines 93 are illustrated, and are equally spaced 15 degrees apart from each other. However, any number of indicator lines 93 may be used and still fall within the confines of the present invention. As best illustrated in FIG. 6, the indicator lines 93 are labeled by reference numerals 95. In the particular embodiment illustrated in FIGS. 6 and 7, the reference numerals 95 designate 15, 30, 45, and 60 degree indicator lines 93.

FIG. 7 illustrates the use of the angle adjustment assembly 84 to adjust the blade angle β by placing the forward ends 27 of the blades 25 against the raised edge 89 with a forward end of a top blade aligned with the origin X. Once the forward ends 27 of the blades 25 are against the raised edge 89, the knife 21 is angled such that the desired blade angle β is achieved. The indicator line 93 which is aligned with an upper surface of the top blade is read to determine the angle β. As described earlier, the desired blade angle β is substantially equal to the hair angle α.

In an alternative embodiment, the raised edge 89 of the rectangular block 91 is made of a magnetic material whereby the blades 25, which are made of a ferromagnetic material, are attracted to the raised edge 89.

Although the pin 73, illustrated in FIG. 4B, and the adjustment block 84 of FIGS. 6 and 7 are illustrated as two different embodiments for shifting the blades 25, the two embodiments may be used separately or in combination. In addition, other mechanisms for shifting the blades are contemplated. For example, the shifting of the blades may be performed by gravity, specially adapted springs, variously shaped magnets, levers, pistons, rods, or other similar apparatus commonly known in the art.

FIGS. 8 and 9 depict a second embodiment of the present invention in which a multiple bladed surgical knife 21' includes a handle 23' having sequential angle markings 317 on an upper surface of the handle extending longitudinally along the length of the handle. The knife 21' according to the second embodiment of FIGS. 8 and 9 includes a pin 303 for adjusting the relative locations of the blades and an indicator arm 305 attached to the pin. The indicator 305, illustrated in FIG. 10, indicates the angle marking 317 corresponding to the blade angle β. The embodiment of FIGS. 8 and 9 operates in a manner similar to the embodiment of FIGS. 2 and 3. However, in the embodiment of FIGS. 8 and 9, the nut 49' is located on the opposite side of the knife 21' as compare to the knife 21 of FIGS. 2 and 3.

The indicator arm 305 and the pin 303 configuration are illustrated in FIG. 10, and include a spring 307, a ball joint 309, a lower pivot 311 and an upper handle 313. As illustrated in FIGS. 8 and 9, the pin 303 includes a pivot 311 which is pivotally connected to the base 35' at a connection 319. The connection 319 may be any of the pivotal connections which are known in the art. As such, the pin 303 functions in a manner similar to the pin 73 of the embodiment of FIGS. 2 and 3, described above in further detail. Thus, the pin 303 may be pivoted about the pivotal connection 319 in the longitudinal direction of the handle 23'. Pivoting of the pin 303 shifts the blade ends 27' in the same manner as the pin 73.

The indicator arm 305 is biased toward the handle 23' by the spring 307. When the pin 303 is rotated about the lower pivot 311, the spring 307 maintains the end of the indicator arm 305 or the pointer 315 in contact or close proximity with the angle markings 317 of the handle 23'. The indicator arm 305 rotates about the ball joint 309 when the surgeon grasps the upper handle 313 and rotates the pin 303 longitudinally along the handle 23'.

The spacers 29' have a pin opening 69' similar to the opening 69 of the embodiment depicted in FIG. 3, except that the pin opening 69' is located towards the handle from the bolt 49'. Thus, when the pin 303 is rotated about the pivot 319, the pointer 315 will indicate the angle marking 317 corresponding to the blade angle β. FIG. 8 illustrates the blades 25 shifted at approximately a 30 degree blade angle position β. FIG. 9 illustrates the blades shifted to the zero degree position. This embodiment of the present invention advantageously permits the surgeon to adjust the blade angle β to a predetermined angle without measuring the blade angle with an external measurement device, or estimating the blade angle without guidance.

As illustrated by FIG. 5, the nut 31 and bolt 49 of the knife 21 are preferably located on a top surface of the knife. Thus, when the knife 21 is used by a surgeon, the nut 31 is not prone to interfere with the scalp and hair because it is located on the side of the knife farthest from the scalp 77. However, the knife 21' of FIG. 8 illustrates that the nut 31' and bolt 49' may be located on an opposite side of the knife and still be within the scope of present invention.

FIG. 11 illustrates a third embodiment of the present invention in which a knife 21" includes a bolt 49" pivotally connected to a base 35" of a handle 23'. The blades 25" and the spacers 29" have openings 333 for receiving the bolt 49" similar to the embodiment of FIGS. 2 and 3. However, located above the spacers 29" and blades 25" is a stationary indicator plate 323. The indicator plate 323 is shaped as a quarter ellipse, with a curved upper edge facing away from the knife 23".

The bolt 49" according to the embodiment of FIG. 11, extends outwardly away from the indicator plate 323 and a lower surface of the nut 31" abuts the curved upper surface of the indicator plate. Because the bolt 49" is pivotally connected at a pivot connection 331 to the base 35'", the bolt rotates in the longitudinal direction of the knife 21" to shift the blades in a manner similar to the pin 73 illustrated in FIGS. 4A and 4B.

The indicator plate 323 contains angular number markings 325, which correspond to the blade angle β. Thus, a surgeon may longitudinally shift the blades with respect to each other by rotating the bolt 49, without having to measure or estimate the blade angle β.

FIG. 12 illustrates a fourth embodiment of the present invention in which a knife 21'" includes a bolt 49'" similar to the bolt 49 of the embodiment shown in FIGS. 2 and 3. However, the bolt 49'" according to the fourth embodiment is angled with respect to the base 35'" such that the blades may be shifted to a greater angle β than the knives of the previous embodiments.

The blades 25 used in all the embodiments of the present invention are preferably of a standard type which are known to be used in the surgical field. Because of the constrains of the standard sized blades 25 having standard sized openings 53, 71, the blades may only be shifted to a 45 degrees blade angle β while still enabling the blade to be secured firmly to the handle 23. However, when the bolt 49'" is angled, as depicted in the embodiment of FIG. 12, the knives may be shifted even further beyond the normal 45 degree blade angle β limit.

In the embodiment depicted in FIG. 12, the bolt 49'" has been angled at an angle of 30 degrees with respect to a line perpendicular to the longitudinal axis of the handle 23'". As such, standard blades 25 may be shifted to blade angles β of 60 degrees with the embodiment depicted in FIG. 12. While the preferred bolt angled in the embodiment of FIG. 12 is 30 degrees, the bolt may be angle at other angles to achieve other blade angles β.

As depicted in FIG. 12, a slip spacer 335 must be placed between the nut 31 and the blades 25'". The slip spacer is not fixed to the nut 31'" or to the bolt 49'" and has an angled lower surface which abuts the blades. As depicted in FIG. 12, the knife 21'" may also be equipped with spacers 29'" having pin openings 69'" for use with a pin 73'", as described above.

Although the previous described embodiments of the present invention use standard blades 25 which are known in the surgical industry, other blades may be used which are not of standard sizes. By using blades of different sizes having differently sized openings 53 and 71, different maximum blade angles β may be achieved without angling the bolt 49'".

The above described embodiments of the present invention are used to remove donor strips from a donor for transplantation to a donee, who are often the same individual. In doing so, a surgeon using the above describe multiple bladed surgical knife would: (1) determine the hair angle α the hair 81 makes with respect to a line perpendicular to the scalp 77, (2) shift the blades 25 to a plurality of positions such that the blade angle β is substantially equal to the hair angle α, (3) insert the blades into the scalp parallel with the hair angle α, (4) translate the blades through the scalp, and finally (5) remove the plurality of hair-laden donor strips from the scalp.

To realize another important benefit of the invention, using the spacer ends to prevent the blades from penetrating the tissue beyond the predetermined blade penetration depth, as described above, a surgeon would also: (1) determine the blade penetration depth d, (2) choose a plurality of spacers 29 for installation into the knife 21, and (3) shift the spacer ends to a plurality of positions located at a distance from each the forward ends of the blades substantially equal to the determined blade penetration depth.

Each of the forgoing observations are results of the present invention. The above description of the preferred embodiments of the present invention must be considered as illustrative only of the principle of the invention and not limitative. Indeed, it may be easily understood that numerous modifications could be made by those skilled in the art without departing from the spirit of the invention as defined in the claims below.

What is claimed is:

1. A surgical knife comprising:
   a handle having a distal end and a proximal end, the distal end including a base;
   a plurality of movable blades removably mounted on the base of the handle, each of the blades having a longitudinal axis and a sharpened forward end;
   a plurality of spacers spacing the blades from each other;
   a securing member removably securing the blades to the handle;
   a shifting mechanism for longitudinally shifting the blades with respect to each other to a plurality of blade positions, the forward ends of the blades forming a first line at a first blade position and a second line at a second blade position.

2. The surgical knife according to claim 1, wherein the first line forms a first angle with respect to the longitudinal axis of the blades, and the second line forms a second angle with respect to the longitudinal axis of the blades.

3. The surgical knife according to claim 2, wherein the shifting mechanism further includes:
   an angle adjustment assembly including a forward face having a base line formed thereon, a raised edge perpendicular to the base line, a plurality of angle indicator lines located on the forward face between the horizontal line and the raised edge, whereby the forward ends of the blades are adjusted to form a line at a plurality of angles with respect to the longitudinal axis of the blades by placing the forward ends of the blades against the raised edge of the angle adjustment assembly.

4. The surgical knife according to claim 3, wherein the raised edge includes a magnetic material whereby ferromagnetic blades are attracted to the raised edge.

5. The surgical knife according to claim 1, wherein each of the spacers further includes a front end and a longitudinal axis, wherein the shifting mechanism longitudinally shifts the spacers with respect to each other to a plurality of spacer positions, the front edges of the spacers forming a first spacer line at a first spacer position and a second spacer line at a second spacer position.

6. The surgical knife according to claim 5, wherein the first spacer line forms an initial angle with respect to the longitudinal axis of the spacers, and the second spacer line forms an angle greater than the initial angle with respect to the longitudinal axis of the spacers.

7. The surgical knife according to claim 5, wherein the each of the front edges of the spacers are located at a predetermined distance from each of the forward ends of the blades, whereby the front edges of the spacers prevents the blades from penetrating tissue beyond the predetermined distance.

8. The surgical knife according to claim 5, wherein the longitudinal axis of the spacers is substantially parallel with the longitudinal axis of the blades.

9. The surgical knife according to claim 1, wherein the spacers and the blades are located parallel to each other.

10. The surgical knife according to claim 1, wherein each of the spacers and the blades further includes an elongated opening extending in a longitudinal direction of the blades and the spacers.

11. The surgical knife according to claim 10, wherein the elongated openings in the blades and the spacers receives the securing member.

12. The surgical knife according to claim 11, wherein the blades and the spacers shift when shifted by the shifting mechanism longitudinally with respect to the securing member.

13. The surgical knife according to claim 1, wherein the securing member includes a screw attached to the base of the handle and a nut threaded on the screw.

14. The surgical knife according to claim 1, wherein the base of the handle includes a recess for receiving a portion of the blades and the spacers within the distal end of the handle.

15. The surgical knife according to claim 1, wherein the shifting mechanism includes a pin extending through openings in the blades and the spacers for adjusting relative positions of the blades.

16. The surgical knife according to claim 15, wherein the base of the handle includes a indentation receiving a tip of the pin and the relative positions of the blades are adjusted by pivoting the pin about the pin tip received in the indentation.

17. The surgical knife according to claim 15, wherein the shifting mechanism further comprises an indicator and a plurality of angle markings on the handle, the indicator indicating a first angle marking corresponding to the first line at the first blade position and indicating a second angle marking corresponding to the second line at the second blade position.

18. The surgical knife according to claim 17, wherein the indicator further includes a spring biasing the indicator toward the handle, wherein the indicator is pivotally connected to the pin.

19. The surgical knife according to claim 15, wherein the pin is removable.

20. The surgical knife according to claim 15, wherein a tip of the pin is pivotally attached to the base of the handle.

21. The surgical knife according to claim 1, wherein the handle further includes a flat portion located substantially near the distal end of the handle which provides a flat surface for application of pressure with a finger.

22. The surgical knife according to claim 1, further including a forward wall abutting a portion of each of the blades and the spacers, the forward wall supporting the blades and the spacers in a shifted position.

23. The surgical knife according to claim 1, further including a forward wall abutting a portion of each of the blades and the spacers, the forward wall preventing rotation of the blades and the spacers.

24. A surgical knife comprising:
a base;
a plurality of parallel blades;
means for securing the blades to the base; and
means for shifting a longitudinal position of the blades with respect to each other and with respect to the base between a first cutting position and a second cutting position, the means for shifting a longitudinal position of the blades includes a pivoting member extending though an opening in each of plurality of parallel blades.

25. A surgical knife comprising:
a base;
a plurality of parallel blades;
means for securing the blades to the base;
means for shifting a longitudinal position of the blades with respect to each other and with respect to the base between a first cutting position and a second cutting position; and
wherein the means for securing the blades to the base and the means for shifting a longitudinal position of the blades comprise a threaded member pivotally connected to the base of the handle and extending through openings in the blades.

26. The surgical knife according to claim 24, further including a forward wall abutting a portion of each of the blades, the forward wall supporting the blades in a shifted position.

27. A method of removing hair-laden tissue from a donor for transplantation to a donee, comprising the steps of:
providing a multiple bladed surgical knife having a base, a plurality of blades, means for securing the blades to the base, and means for shifting a longitudinal position of the blades with respect to each other and with respect to the base;
determining a hair angle between a direction of hair growth and a line perpendicular to a scalp;
shifting the blades to a plurality of positions whereby a line formed by a forward end of each of the blades is orientated at a blade angle with respect to a line perpendicular to a longitudinal axis of the knife, the blade angle being substantially equal to the hair angle;
inserting the blades into the scalp at a direction parallel to the direction of hair growth;
translating the blades through the scalp; and
removing a plurality of hair-laden tissue strips from the scalp.

28. The method according to claim 27, further comprising the steps of:
determining a blade penetration depth;
choosing a plurality of spacers;
positioning one of the spacers between each of said blades;
shifting the plurality of spacers to a plurality of spacer positions whereby a distal end of each of the plurality of spacers is located a distance from each the forward ends of the blades substantially equal to the determined blade penetration depth, whereby the spacer ends prevent the blades from penetrating the tissue beyond the determined blade penetration depth.

* * * * *